(12) United States Patent
Zillmer et al.

(10) Patent No.: US 7,826,054 B2
(45) Date of Patent: Nov. 2, 2010

(54) FUEL CELL INSTRUMENTATION SYSTEM

(75) Inventors: Andrew J. Zillmer, Woodland Hills, CA (US); Joseph P. Carroll, Moorpark, CA (US)

(73) Assignee: Pratt & Whitney Rocketdyne, Inc., Canoga Park, CA (US)

( * ) Notice: Subject to any disclaimer, the term of this patent is extended or adjusted under 35 U.S.C. 154(b) by 664 days.

(21) Appl. No.: 11/744,229

(22) Filed: May 4, 2007

(65) Prior Publication Data

US 2010/0028725 A1 Feb. 4, 2010

(51) Int. Cl.
*G01J 3/28* (2006.01)
(52) U.S. Cl. ...................................... 356/328
(58) Field of Classification Search ................. 356/328, 356/437; 250/339.13, 339.06–339.07; 429/61, 429/90
See application file for complete search history.

(56) References Cited

U.S. PATENT DOCUMENTS

| | | | |
|---|---|---|---|
| 4,058,482 A | 11/1977 | Barls et al. | |
| 4,064,322 A | 12/1977 | Bushnell et al. | |
| 4,128,701 A | 12/1978 | Maricle | |
| 4,259,302 A | 3/1981 | Katz et al. | |
| 5,294,232 A | 3/1994 | Sakairi et al. | |
| 5,329,353 A * | 7/1994 | Ichimura et al. | 356/328 |
| 5,517,314 A | 5/1996 | Wallin | |
| 5,621,213 A * | 4/1997 | Barshad | 356/437 |
| 5,815,276 A | 9/1998 | Fry | |
| 6,396,056 B1 * | 5/2002 | Lord et al. | 250/339.09 |
| 6,528,791 B1 * | 3/2003 | Williams et al. | 250/339.13 |
| 6,579,331 B1 | 6/2003 | Ho | |
| 6,946,215 B2 | 9/2005 | Roy | |
| 7,014,942 B2 | 3/2006 | Gorte et al. | |
| 7,029,778 B1 | 4/2006 | Benson et al. | |
| 7,108,934 B2 | 9/2006 | Narayanan et al. | |
| 7,163,758 B2 | 1/2007 | Steinberg | |
| 2004/0058488 A1 | 3/2004 | Arno | |
| 2004/0138499 A1 | 7/2004 | Buschulte et al. | |
| 2008/0088821 A1 * | 4/2008 | Hurvitz et al. | 356/51 |
| 2008/0173817 A1 * | 7/2008 | Goldstein et al. | 250/338.1 |
| 2009/0207413 A1 * | 8/2009 | Carpenter et al. | 356/437 |

FOREIGN PATENT DOCUMENTS

| | | |
|---|---|---|
| DE | 102004007953 | 9/2005 |
| JP | 57108640 | 7/1982 |
| JP | 2001108614 | 4/2001 |

OTHER PUBLICATIONS

European Search Report mailed Nov. 27, 2008.
Partial European Search Report, mailed Aug. 29, 2008.

\* cited by examiner

*Primary Examiner*—Kara E Geisel
(74) *Attorney, Agent, or Firm*—Carlson, Gaskey & Olds PC

(57) ABSTRACT

An instrumentation system utilizes a single light source collimated through windows through a gas line in communication with a fuel cell. As each beam passes through each window, the gas stream will attenuate each beam. A diffraction grating disperses each attenuated beam and transmits particular wavelength bands through a focusing system to a detector. The measured concentration in the gas stream may then be utilized by a controller to determine the amount of power produced by the cell, determine potential leaks, or determine incomplete reaction.

15 Claims, 1 Drawing Sheet

FUEL CELL INSTRUMENTATION SYSTEM

BACKGROUND OF THE INVENTION

The present invention relates to a fuel cell, and more particularly to an optical instrumentation system therefor.

There are several different general types of fuel cells which can be distinguished one from another primarily by the electrolytes they utilize. For example, there are fuel cells which utilize phosphoric acid, sulfuric acid, fluorinated phosphoric, sulfuric acid or the like acid electrolytes; ion exchange electrolytes; molten carbonate salt electrolytes; solid electrolytes such as doped zirconia or ceria; alkaline electrolytes; and other electrolytes which can be used in the electrochemical electricity-producing reaction. These fuel cells typically use hydrogen as the anode reactant and oxygen as the cathode reactant. However, other elements can be used, such as carbon for an anode reactant and air or chlorine for cathode reactants. The hydrogen will typically come from a fossil fuel which has been catalytically converted to a hydrogen-rich fuel gas, and the oxygen will come from air passed over the cathode side of the cell or cell stack.

Some fuels cells such as molten salt carbonate fuel cells have efficiencies as high as 70%. However, these fuel cells operate at high temperatures which may complicate thermocouple instrumentation of the fuel cell. At such high temperatures, thermocouples may have a relatively short lifespan. Should the thermocouples fail, information regarding the fuel cell operating conditions may become unavailable such that fuel cell may need to be shut down prior to the full lifespan of the fuel cell.

Accordingly, it is desirable to provide a reliable instrumentation system which operates at high temperatures for the full lifetime of the fuel cell.

SUMMARY OF THE INVENTION

The instrumentation system according to the present invention utilizes a gas such as $CO_2$ exhausted from the fuel cell. A gas line from the fuel cell includes windows through the diameter of the line. A single light source is positioned and collimated to direct a collimated beam through each window in the line. As the beam passes through the window, each beam will be attenuated by the gas stream. A diffraction grating then disperses the beam and transmits particular wavelength ranges through a focusing system to a detector which records concentrations at the particular wavelengths in the gas stream. The concentration at the particular wavelengths in the gas stream are utilized to determine the amount of power produced by the cell since the reaction of carbon and oxygen results in a set amount of energy. Lines for oxygen and carbon monoxide CO may also be observed to determine potential leaks (oxygen) or incomplete reaction (CO).

The present invention therefore provides a reliable instrumentation system which operates at high temperatures for the full lifetime of the fuel cell.

BRIEF DESCRIPTION OF THE DRAWINGS

The various features and advantages of this invention will become apparent to those skilled in the art from the following detailed description of the currently disclosed embodiment. The drawings that accompany the detailed description can be briefly described as follows.

DETAILED DESCRIPTION OF THE DISCLOSED EMBODIMENT

Figure 1:
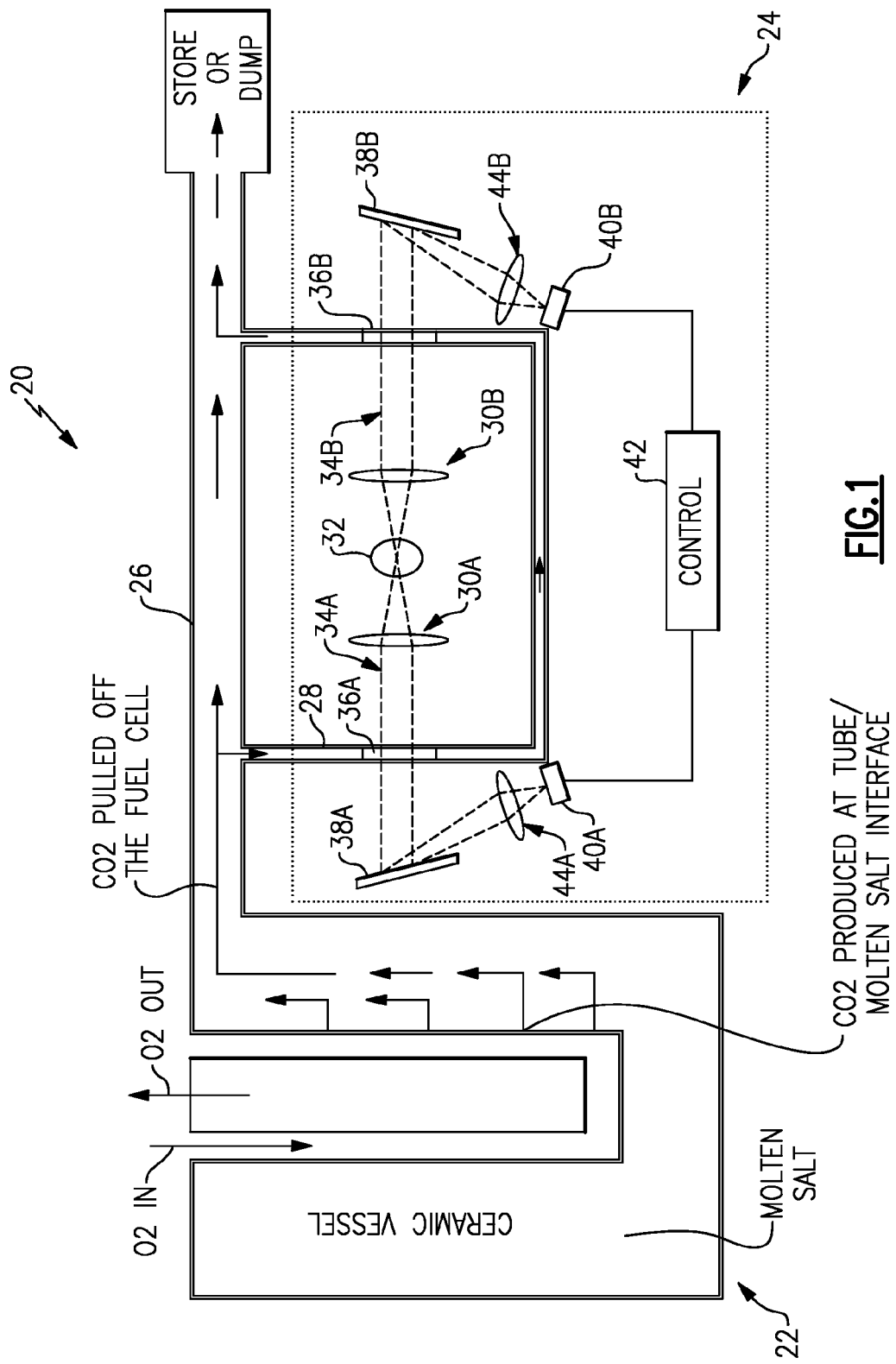
FIG. 1 is a general block diagram view of a fuel cell system with an instrumentation system according to the present invention.

FIG. 1 schematically illustrates a fuel cell system 20 including a fuel cell vessel 22 and an instrumentation system 24. The fuel cell 22 may be any of several different general types of fuel cells distinguished one from another primarily by the electrolytes, cathode reactants, and anode reactants utilized. In the disclosed embodiment, a high temperature direct carbon fuel cell which operates above 1000 F and often between 1400 to 1700 F is described. It should be understood that although a particular component arrangement is disclosed in the illustrated embodiment, other arrangements will benefit from the instant invention.

The fuel cell 22 includes an electrolyte that receives oxygen through a cell or cells within a ceramic tube surrounded by an electrolyte. A liquid anode, such as a molten salt that has a carbon fuel distributed in it surrounds the lower portion of the ceramic tube. The molten salt is contained by a ceramic vessel. The fuel cell 22 splits apart the molecular oxygen into atomic oxygen and generates a current because the atomic oxygen will pass through the cell and will combine with carbon that is dissolved within the molten salt. The oxygen combines with the carbon and generates $CO_2$. The $CO_2$ in the molten salt does not dissolve and is exhausted from the fuel cell 22 through a gas line 26 where it is stored or dumped overboard as generally understood. It should also be understood that although $CO_2$ is disclosed in the illustrated embodiment, other fuel cell arrangements may communicate other gases therefrom, for example, a methane or methanol fuel cell would communicate water vapor instead of $CO_2$ which will likewise be identifiable by the instrumentation system 24.

The instrumentation system 24 communicates with the fuel cell 22 through the exhaust line 26 either directly or through a tap-off line 28 as illustrated. Generally, the instrumentation system 24 communicates either with the exhaust line 26 or the tap-off line 28 depending on the quantity of $CO_2$ generated by the particular fuel cell 22.

The instrumentation system 24 generally includes a collimator system 30A, 30B in optical communication with a single light source 32 such as a glowing filament, laser, LED, etc. The collimator system 30 collimates light source 32 into a collimated beam 34A. Additional collimators can be used to create additional collimated beams, 34B. Each collimated beam 34A, 34B is directed from the light source 32 through a respective window 36A, 36B within the tap-off line 28. That is, the collimated beam 34A, 34B is passed completely through the tap-off line 28 by communication through each respective window 36A, 36B. As the collimated beam 34A, 34B passes through the window 36A, 36B, the collimated beams 34A, 34B will be attenuated by the gas stream through the tap-off line 28.

Subsequent to each collimated beam 34A, 34B being attenuated through the respective window 36A, 36B, each attenuated collimated beam 34A, 34B is diffracted off of a diffraction grating 38A, 38B onto a respective detector 40A, 40B. Each diffraction grating 38A, 38B disperses the beam through a focus system 44A, 44B and transmits only a particular wavelength range—such as a strong $CO_2$ wavelength band (~2 microns wavelength) and a weak $CO_2$ wavelength band (~1 micron wavelength) in the disclosed embodiment— to the respective detector 40A, 40B. The diffraction grating transmits only the particular wavelength band and causes a dispersion that spreads the wavelength band over the detector 40A, 40B such that attenuation of that particular wavelength band is readily identified and measured. It should be understood that the diffraction grating may be utilized to transmit any desired wavelength band. Since only a single light source is utilized, all calibrations issues are essentially eliminated and an accurate relationship is assured.

The respective detector 40A, 40B identifies the concentration of $CO_2$ in the particular wavelength band regions in the gas stream. A controller 42 in communication with each detector 40A, 40B determines the amount of power produced by the fuel cell from the identified concentrations of $CO_2$ since the reaction of carbon and oxygen results in a set amount of energy. That is, the heat produced by the fuel cell 22 (and electrical power) will be proportional to $CO_2$ produced such that $CO_2$ concentration in the tap-off line 28 facilitates an estimate of $CO_2$ concentration in the $CO_2$ exhaust line 26 and thus the amount of $CO_2$ being produced by the fuel cell. This facilitates determination of the fuel cell power level and likely cell temperatures within the fuel cell 22.

The instrumentation system 24 thereby facilitates continuous determination of the power produced by the fuel cell 22. For example, the instrument system 24 may monitor a base $CO_2$ load which would be continuously checked by the controller 42 to identify any issues with the fuel cell 22 by identification of a $CO_2$ decrease. The instrumentation system 24 may also facilitate performance monitoring as power level is related to $CO_2$ production.

It should be understood that collimated beams may alternatively or additionally be utilized to detect oxygen and carbon monoxide to, for example, determine potential leaks (oxygen) or incomplete reaction (carbon monoxide).

It should be understood that relative positional terms such as "forward," "aft," "upper," "lower," "above," "below," and the like are with reference to the normal operational attitude of the vehicle and should not be considered otherwise limiting.

Although particular step sequences are shown, described, and claimed, it should be understood that steps may be performed in any order, separated or combined unless otherwise indicated and will still benefit from the present invention.

The foregoing description is exemplary rather than defined by the limitations within. Many modifications and variations of the present invention are possible in light of the above teachings. The disclosed embodiments of this invention have been disclosed, however, one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. A fuel cell system comprising:
    a fuel cell;
    a gas line in communication with said fuel cell, said gas line having a first window and a second window;
    a light source;
    a collimator system to collimate a beam from said light source into a first collimated beam directed through said first window and a second collimated beam directed through said second window;
    a first diffraction grating through which said first collimated beam passes subsequent to passage through said first window;
    a first focus system to focus said first collimated beam which has passed through said first diffraction grating on a first detector to receive said first collimated beam focused by said first focus system;
    a second diffraction grating through which said second collimated beam passes subsequent to passage through said second window;
    a second focus system to focus said second collimated beam which has passed through said second diffraction grating; and
    a second detector to receive said second collimated beam focused by said second focus system.

2. The system as recited in claim 1, wherein said first diffraction grating disperses the first collimated beam and transmits a first wavelength band and said second diffraction grating disperses the second collimated beam and transmits a second wavelength band, said first wavelength band different than said second wavelength band.

3. The system as recited in claim 1, further comprising a controller in communication with said first detector and said second detector.

4. The system as recited in claim 1, wherein the gas line is a tap-off line.

5. The system as recited in claim 1, wherein said first detector detects carbon dioxide gas of an approximately 2 micron wavelength band and said second detector detects carbon dioxide gas of an approximately 1 micron wavelength band.

6. A method of instrumenting a fuel cell comprising the steps of:
    (A) collimating light from a single light source into a first collimated beam and a second collimated beam;
    (B) directing the first collimated beam through a first window in a gas line in communication with a fuel cell;
    (C) directing the second collimated beam through a second window in the gas line in communication with the fuel cell;
    (D) receiving the first collimated beam at a first detector subsequent to said step (B); and
    (E) receiving the second collimated beam at a second detector subsequent to said step (C).

7. A method as recited in claim 6, wherein said step (D) comprises the step of:
    (a) directing the first collimated beam onto a first diffraction grating prior to receiving the first focused beam at the first detector;
    (b) communicating with the first detector; and
    (c) identifying the concentration of a gas communicated through the gas line at a wavelength band defined by the first diffraction grating.

8. A method as recited in claim 6, wherein said step (E) comprises the step of:
    (a) directing the second collimated beam onto a second diffraction grating prior to receiving the second focused beam at the second detector;
    (b) communicating with the second detector; and
    (c) identifying the concentration of a gas communicated through the gas line at a wavelength band defined by the second diffraction grating.

9. A method as recited in claim 6, further comprising the step of:
    (F) communicating with the first and second detector; and
    (G) determining a fuel cell power level from said step (F).

10. A method as recited in claim 6, further comprising the step of:
    (F) communicating with the first and second detector; and
    (G) determining a $CO_2$ concentration at a first and second wavelength in a gas stream communicated through the gas line.

11. A method as recited in claim 6, further comprising the step of:

(F) communicating with the first detector; and (G) determining a quantity of CO in a gas stream communicated through the gas line.

12. A method as recited in claim 6, further comprising the step of:

(F) communicating with the first detector; and (G) determining a quantity of $O_2$ in a gas stream communicated through the gas line.

13. The system as recited in claim 1, wherein said gas line having said first window and said second window is an exhaust line from said fuel cell.

14. The system as recited in claim 1, further comprising an exhaust line from said fuel cell, said gas line having said first window and said second window a tap-off line from said exhaust line.

15. The system as recited in claim 1, wherein said controller is operable to determine power produced by the fuel cell from identified concentrations of $CO_2$.

* * * * *